United States Patent [19]
Shu

[11] Patent Number: 5,323,784
[45] Date of Patent: Jun. 28, 1994

[54] HEART RATE CALCULATION FOR USERS OF EXERCISE MACHINES

[75] Inventor: Stephen K. Shu, Fountain Valley, Calif.

[73] Assignee: Unisen, Inc., Tustin, Calif.

[21] Appl. No.: 861,949

[22] Filed: Apr. 2, 1992

[51] Int. Cl.$^5$ ............................................. A61B 5/024
[52] U.S. Cl. .................................. 128/707; 128/706; 482/54; 482/902
[58] Field of Search .................... 128/706, 707; 482/8, 482/9, 52, 54, 57, 900, 901, 902

[56] References Cited

U.S. PATENT DOCUMENTS

| | | | |
|---|---|---|---|
| 3,667,213 | 6/1972 | Ensign | 58/126 R |
| 3,717,140 | 2/1973 | Greenwood | |
| 3,773,038 | 11/1973 | Smith et al. | 128/706 |
| 4,058,118 | 11/1977 | Stupay et al. | |
| 4,181,134 | 1/1980 | Mason et al. | 128/706 |
| 4,248,244 | 2/1981 | Charnitski et al. | 128/706 |
| 4,295,472 | 10/1981 | Adams | 128/690 |
| 4,319,581 | 3/1982 | Cutter | 128/707 |
| 4,572,207 | 2/1986 | Yoshimi et al. | 128/706 |

OTHER PUBLICATIONS

Ludwig, "Heart- or respiration-rate calculator", Med. & Biol. Eng. & Comput. 1977 15, pp. 700–702.

Philip, "Improvement in Rate Determination Using A New Method Based on Occurence Times", AAMI 17th Annual Meeting, May 9-12, 1982 San Francisco, CA.

Nijhawan et al., "A Beat-to-Beat Heart Rate Meter", IEEE Transactions on Biomed. Eng. vol. BME-28 #1 Jan. '81.

Primary Examiner—Lee S. Cohen
Assistant Examiner—Jeffrey R. Jastrzab
Attorney, Agent, or Firm—Daniel L. Dawes

[57] ABSTRACT

A simple heart rate calculation process is incorporated into an exercise machine. The user controls the process by counting his/her own pulse. With the exercise machine temporarily stopped, the user finds his/her pulse with one hand, and pushes a start/stop button with the other hand. The button is pushed to stop on a count of one, and then pushed to stop on a predetermined count, e.g., 10. An embedded device automatically calculates and displays the user's heart rate.

7 Claims, 4 Drawing Sheets

HEART RATE CALCULATION FOR USERS OF EXERCISE MACHINES

BACKGROUND OF THE INVENTION

This invention relates to the field of exercise machines, and specifically to a simplified heart rate calculator which permits the user of an exercise machine (operator) to determine his/her current heart rate, in order to judge the aerobic progress of the exercise.

One of the primary goals of aerobic exercising is to permit the user to obtain a temporary heart rate increase. This is considered desirable as a method of improving physical fitness. However, it is not desirable to drive the heart rate to an excessive level.

Exercise machines often incorporate heart rate monitors, which permit the user to learn his/her current heart rate during the exercise regimen. Heretofore, the devices used have been designed to engage the body of the user in a location where a pulse is available, such as the wrist or neck. The device counts the pulses and calculates the pulse rate, which is available for display.

The most common practice is a crude approach, in which the user leaves the exercise machine, and then counts his/her pulse while looking at a nearby clock or watch. The general practice is either to count the pulse for 15 seconds and then multiply the count by 4, or to count for 30 seconds and multiply by two.

Either of the two heart rate determining techniques just discussed has significant limitations. The counting and calculating by the user is not very accurate because of the need both to synchronize the pulse counting with the observed clock or watch, and to make the correct calculation. It also requires taking a count over a relatively long period if reasonable accuracy is desired.

The heart rate monitors which engage the body to automatically count the pulses have not been very satisfactory. Under the conditions of normal aerobic exercising, they have great difficulty in accurately sensing the heart beat. The ease or difficulty of sensing the heart beat varies from person to person. Some individuals have heart beats which are almost impossible to sense without the use of electrodes. Furthermore, the environment may cause interference which tends to cause sensor inaccuracy.

SUMMARY OF THE INVENTION

The present invention provides a simple solution of the problem. The operator is relied on to feel and count his/her own pulse. A predetermined number of pulses is used. At the beginning count, the operator pushes a button (switch) in synchronization with the first pulse. When the selected number of pulses has occurred, the operator pushes the button (switch) in synchronization with the counted pulse. For example, the switch may be pushed on pulse no. 1 and again on pulse no. 10, thus recording the total length of 9 pulse-to-pulse intervals.

The pulse rate calculation is done automatically by an electronic digital calculator embedded in the exercise machine. The calculated result is shown on the display panel of the machine.

The result is a very simple and very accurate pulse rate determination, which is obtained very quickly. No heart beat sensor is required.

DETAILED DESCRIPTION OF SPECIFIC EMBODIMENTS

Figure 1:
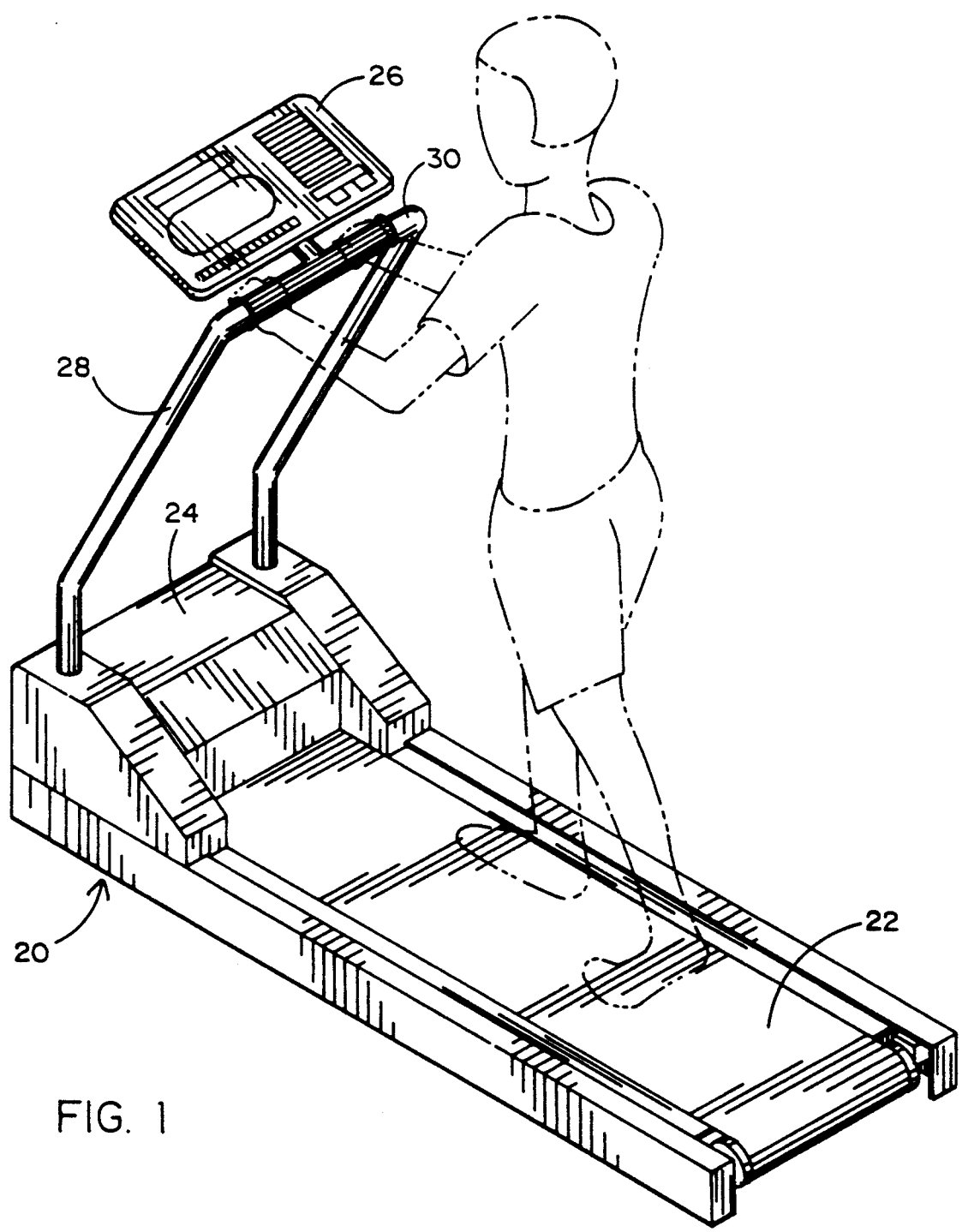
FIG. 1 is an isometric view of a treadmill, one of many types of exercise machines for which the heart rate calculator is intended.

As stated above, the heart rate calculator may be used in any environment, and may be associated with any exercise machine. For example, as shown in FIG. 1, it may be associated with a treadmill, or running machine, 20. The treadmill has a running/walking surface 22, which is provided by an endless belt. An enclosure 24 located at the front of the treadmill houses the driving motor, whose speed is variable at the will of the user. A display panel 26 is mounted on the top of a front rail 28, which is in the shape of an inverted "U", and which provides a hand rail 30 for the user to grip if necessary.

Figure 2:
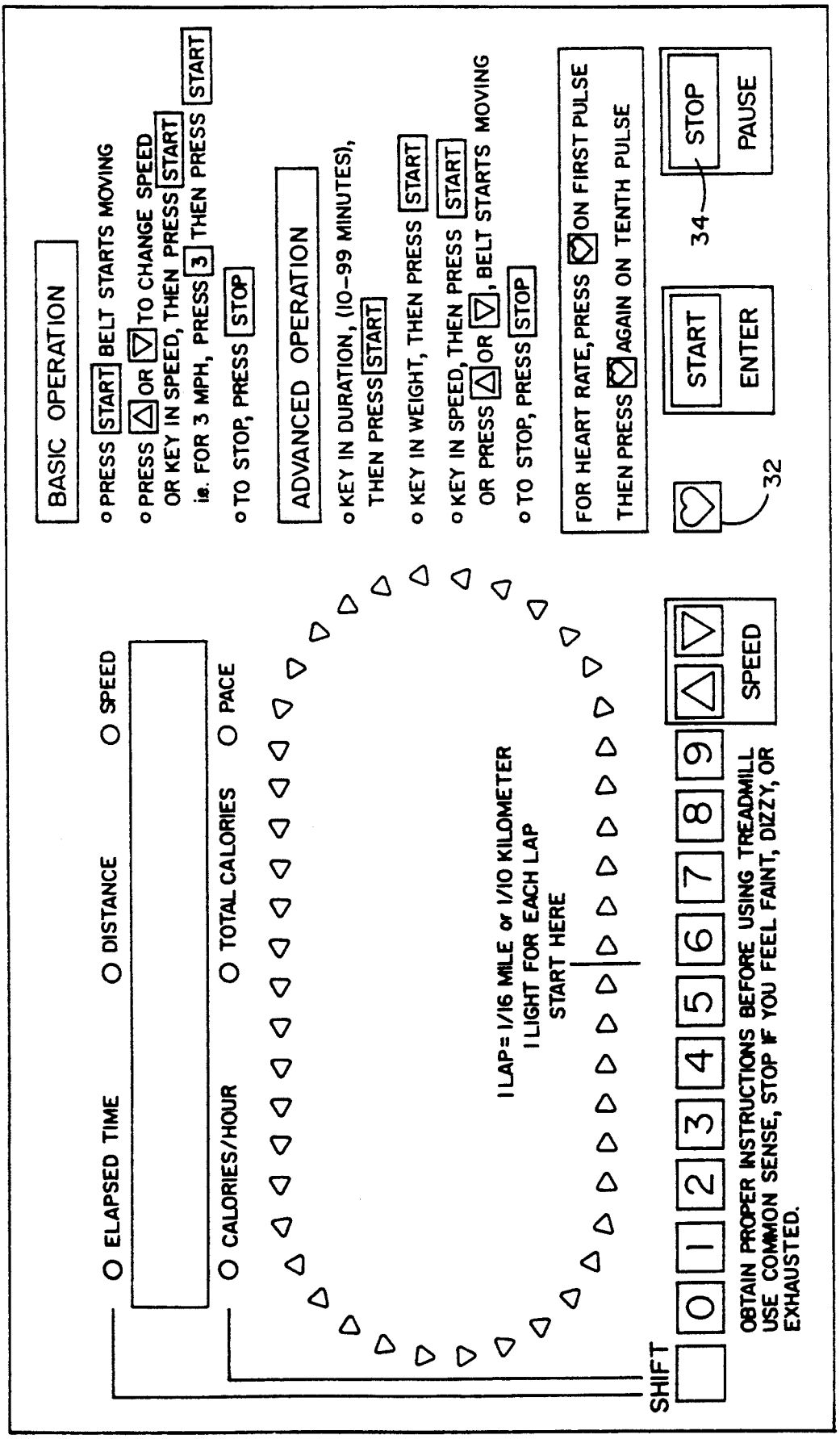
FIG. 2 is a plan view of a typical exercise machine display panel, in which the control switch for the heart rate calculator is included.

A close-up of a particular display unit is shown in FIG. 2. The display unit usually encloses a microcomputer, which translates user commands into treadmill control, and which receives treadmill feedback information. This information is used both to control the treadmill and to provide a visual display for the user. As shown, the display panel has both LED display elements and switch control elements to enter the user's commands.

The item of interest in this description is the switch, or button, 32 which has a heart-shaped symbol. The treadmill stop switch 34 is also involved (usually) in operation of the heart rate calculator. The switch 32 is pushed once to start the heart rate calculator and is pushed a second time to stop the heart rate calculator.

Because the user requires the use of both hands to check his/her heart rate, normally the stop switch 34 will be pushed to cause the exercise machine to pause during heart rate calculation.

The user first uses one hand to locate an easily readable pulse, preferably in the neck, although the pulse in the wrist may be used. The user pushes the start/stop switch 32 synchronously with his/her count of pulse no. 1; and the user again pushes the start/stop switch 32 synchronously with his/her count of pulse no. 10. This provides a total elapsed time of nine pulse-to-pulse intervals for use by the heart rate calculator. Any desired number of pulses could be used by the heart rate calculator. The selection of a nine interval count is considered desirable because it combines quickness with accuracy. Reduced intervals would be quicker but less accurate. Increased intervals would be more accurate but more delayed. The number of intervals used is a matter of designer choice.

Figure 3:
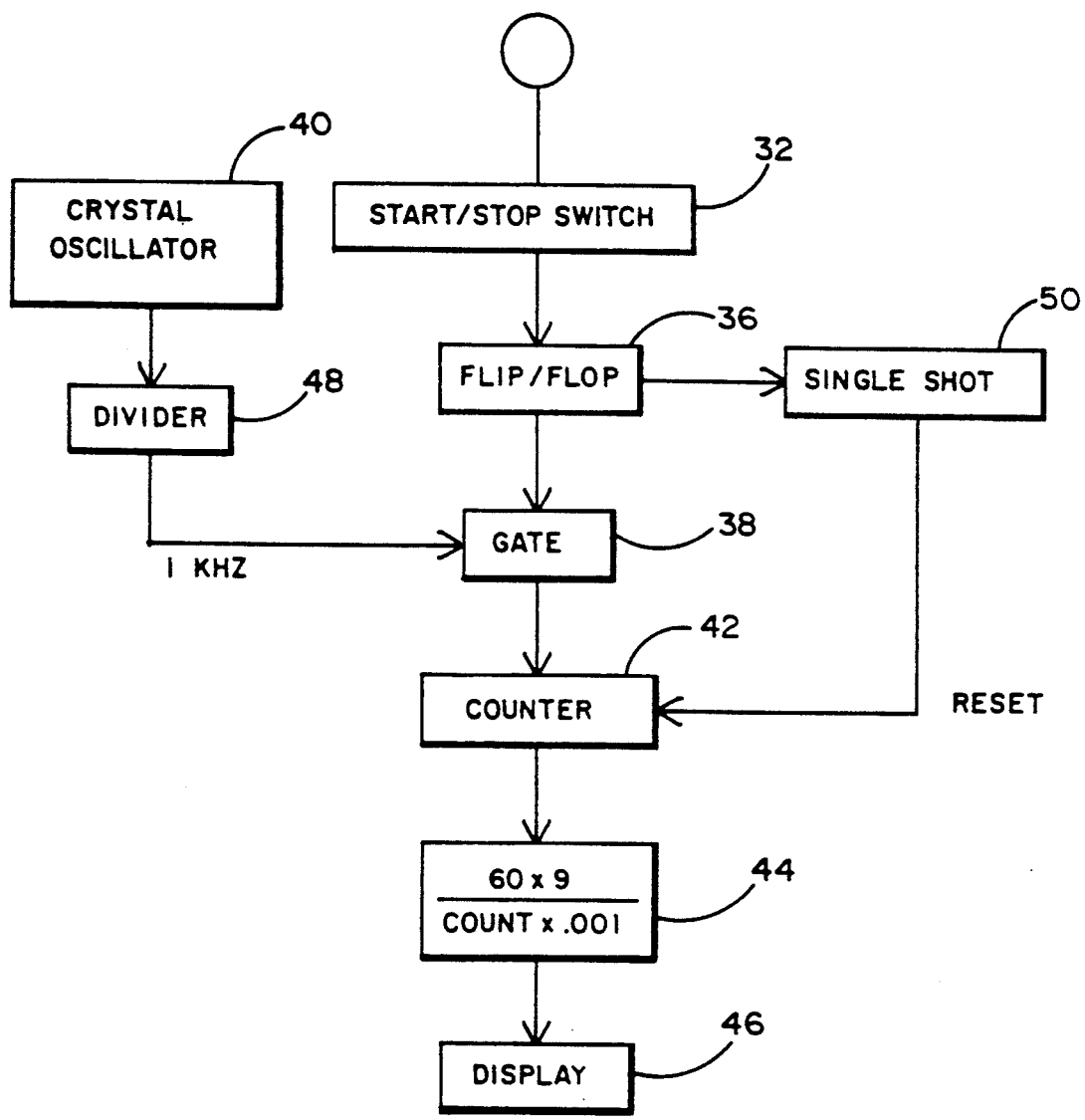
FIG. 3 is a block diagram showing the calculation procedure used in determining the heart rate based on the user's pulse readings.

The FIG. 3 block diagram shows the simple mechanization needed to provide the heart rate calculation, based on the user's pushing of the start/stop switch 32. When the switch is first pushed, it activates a flip/flop 36 which causes a gate 38 to open. This allows clock increments from a crystal oscillator 40 to pass through gate 38 to counter 42. The number in counter 42 is fed to calculator 44, in which the number in the counter is converted into a number representing the user's heart rate. This heart rate is shown on the display panel 46 in numerical form, using the three most significant numbers. If the heart rate is below 100, the display will show one number after the decimal. If the heart rate is 100 or more, the display will be in integers. Greater precision would be useless.

The use of the crystal oscillator 40 as a clock provides extreme counting accuracy. In order to reduce the frequency of the clock to 1 kilohertz, a divider 48 is used.

When the start/stop switch 32 is pushed by the user the second time, flip/flop 36 closes gate 38, thus freezing the number registered in counter 42 and in calculator 44. The goal is to determine beats per minute. Dividing the number of beats (9) by the total time measured by the counter [number of counts × the length of each count (0.001 second)] gives the heart rate per second. Multiplying by 60 converts the value to heart rate per minute, which is the desired information. The numerical display of this information provides a clear and highly accurate indication to the user of his/her heart rate. The user may then decide whether to continue or to conclude the exercise.

After each completion of a heart rate calculation, the return of the flip/flop 36 to its off position causes a single shot 50 to reset counter 42 to zero. In other words, the second push by the user on switch 32 causes the counter gate 38 to close and then resets the counter 42.

Figure 4:
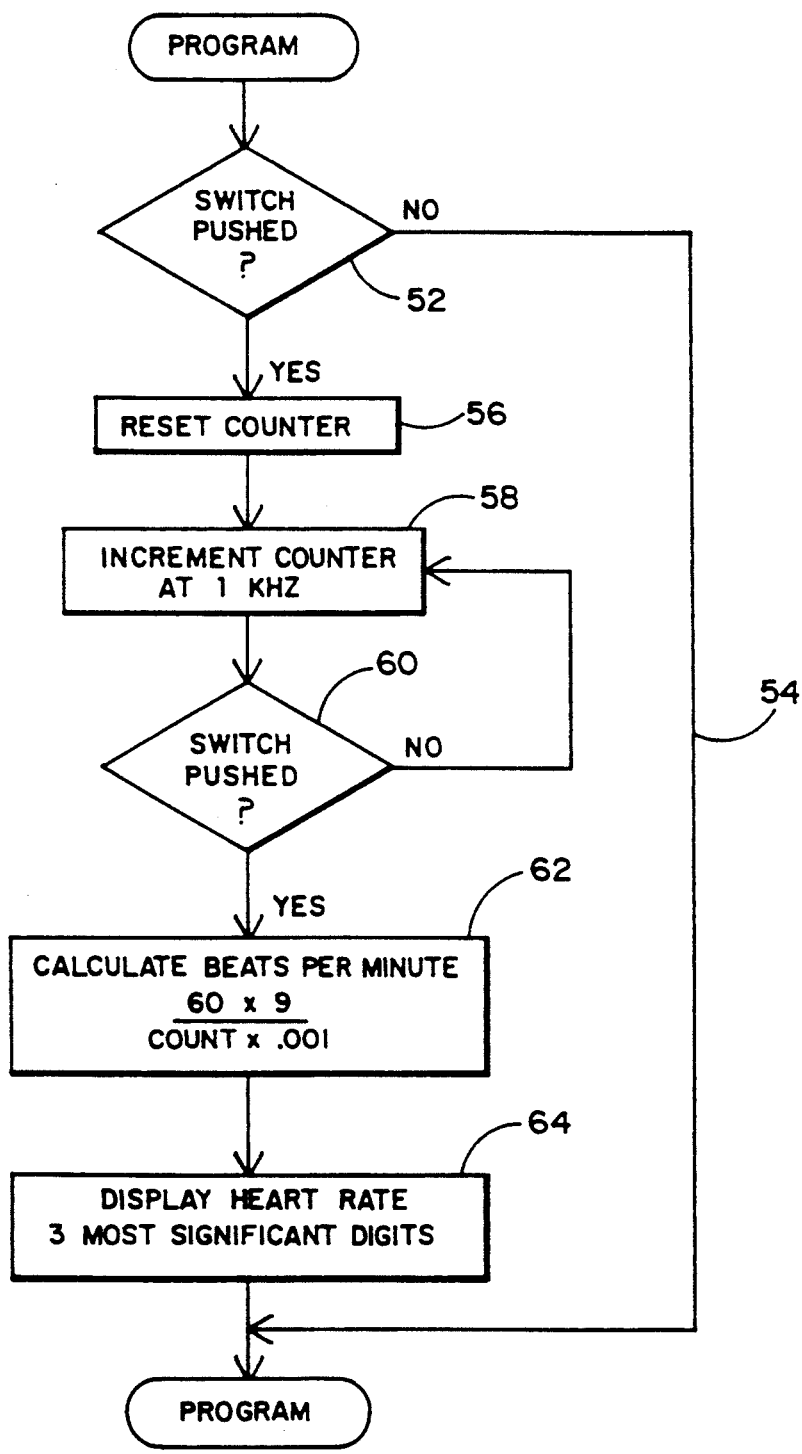
FIG. 4 is a flow chart showing the software steps used in the heart rate determination, if a computer is available.

FIG. 4 shows a software flow chart used where a microcomputer is already available in the exercise machine, which is the case with most modern machines. A 1 kilohertz interrupt service routine is assumed.

At a decision block 52, the question is answered whether the stop/start switch 32 (in FIG. 2) has been pushed. A negative answer recirculates the control flow on line 54.

A positive answer at block 52 causes the counter to be reset at process block 56, and also causes the counter to be incremented at process block 58. The control flow is to decision block 60, which checks whether the switch 32 has been pushed a second time to end the count. As long as the answer is negative, the process block 58 causes the counter to continue incrementing.

When the answer at block 60 is "yes", the control flows to process blocks 62 and 64. The heart rate is calculated at block 62 and is caused to be displayed by block 64. The counter ceases to increment because block 60 has cut it off. Resetting of the counter will be the first process when the next start push occurs at switch 32.

The present invention is a very simple and accurate heart rate device for the users of exercise machines. While it requires their participation in the process, it has proved to be extremely popular with users. One of its major advantages is that no pulse sensor is required, except the user. It is surprising that this "no frills" approach to heart rate monitoring in the field of aerobic exercise machines has provided the answer sought for many years by many designers and producers of such machines.

From the foregoing description, it will be apparent that the apparatus and method disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. A method of heart rate calculation including the steps of:
   (a) providing an aerobic exercise machine having a display panel operable by a user;
   (b) establishing an initial heart pulse signal by contiguous interface of a first hand of said user with a predetermined body portion of said user;
   (c) substantially simultaneously initially actuating a calculation switch member located on said display panel with a second hand of said user;
   (d) initiating a calculation circuit for providing a clocking signal count responsive to said actuation of said calculation switch member on said display panel by said user;
   (e) counting a predetermined number of said heart pulse signals sensed by said first hand of said user;
   (f) secondarily actuating said calculation switch member on said display panel when said predetermined number of said heart pulse signals is sensed by said user for calculation of a heart beat rate by said calculation circuit; and,
   (g) displaying said heart beat rate on said display panel.

2. The method of heart rate calculation as recited in claim 1 where the step of initiating said calculation circuit is followed by the steps of:
   (a) providing an automatic clocking signal; and,
   (b) initiating said clocking signal count.

3. The method of heart rate calculation as recited in claim 2 where the step of secondarily actuating said calculation switch member is followed by the steps of:
   (a) terminating said clocking signal count; and,
   (b) converting said clocking signal count to an indicia representative of said heart beat rate.

4. The method of heart rate calculation as recited in claim 3 where the step of terminating said clocking signal count is followed by the steps of:
   (a) closing a gate of said calculation circuit for disconnecting a counter circuit; and,
   (b) terminating incrementation of said counter circuit.

5. The method of heart rate calculation as recited in claim 2 where the step of initiating said clocking signal count includes the steps of:
   (a) opening a gate of said calculation circuit for connecting a counter circuit to said clocking signal; and,
   (b) resetting said counter circuit.

6. The method of heart rate calculation as recited in claim 1 where the step of establishing an initial heart pulse signal is preceded by the step of terminating operation of said aerobic exercise machine.

7. An exercise machine heart rate calculation system, comprising:
   (a) an exercise machine having a display panel mounted thereon and operable by a user;
   (b) heart rate calculation means for calculating a heartbeat rate of a user located within said display panel;
   (c) switch means for actuating and deactuating said heart rate calculation means, said switch means defining a singular switch member located on said display panel and electrically connected to said heart rate calculation means, said switch member being initially actuated simultaneously with said user detection of a first heartbeat and secondly actuated simultaneously with said user detection of a predeterminedly numbered heartbeat, said heart rate calculation means including means for providing an incremented clocking signal, means for counting said incremented clocking signal to provide a clocking count for said predetermined number of said heartbeats and means for conversion of said clocking count into a heart rate; and, (d) display means on said display panel for displaying said heart rate.

* * * * *